US007553805B2

(12) United States Patent
Tichy et al.

(10) Patent No.: US 7,553,805 B2
(45) Date of Patent: Jun. 30, 2009

(54) METHODS AND COMPOSITIONS FOR TREATING VIRAL, FUNGAL, AND BACTERIAL INFECTIONS

(75) Inventors: Daryl J. Tichy, Orem, UT (US); Brian G. Larson, Alpine, UT (US)

(73) Assignee: Solutions Biomed, LLC, Orem, UT (US)

( * ) Notice: Subject to any disclaimer, the term of this patent is extended or adjusted under 35 U.S.C. 154(b) by 143 days.

(21) Appl. No.: 11/514,722

(22) Filed: Aug. 31, 2006

(65) Prior Publication Data
US 2007/0059255 A1 Mar. 15, 2007

Related U.S. Application Data

(63) Continuation-in-part of application No. 11/361,665, filed on Feb. 24, 2006, now Pat. No. 7,351,684, application No. 11/514,722, which is a continuation-in-part of application No. 11/361,836, filed on Feb. 24, 2006, and a continuation-in-part of application No. 11/361,841, filed on Feb. 24, 2006, and a continuation-in-part of application No. 11/361,837, filed on Feb. 24, 2006.

(60) Provisional application No. 60/656,723, filed on Feb. 25, 2005.

(51) Int. Cl.
*C11D 7/18* (2006.01)
*C11D 3/48* (2006.01)

(52) U.S. Cl. .................. 510/372; 510/161; 510/199; 510/235; 510/238; 510/302; 510/309; 510/319; 510/362; 510/370; 510/367; 510/375; 510/382

(58) Field of Classification Search ............ 510/372, 510/161, 199, 235, 238, 302, 309, 319, 362, 510/370, 367, 375, 382
See application file for complete search history.

(56) References Cited

U.S. PATENT DOCUMENTS

| | | | |
|---|---|---|---|
| 716,077 A | 12/1902 | Morrin | |
| 734,467 A | 7/1903 | Martien | |
| 2,103,999 A | 12/1937 | Muller et al. | |
| 2,304,104 A | 12/1942 | Kiabunde et al. | |
| 4,021,338 A | 5/1977 | Harkin | |
| 4,297,298 A | 10/1981 | Crommelynch et al. | |
| 4,311,598 A * | 1/1982 | Verachtert | 210/757 |
| 4,321,255 A | 3/1982 | Boden | |
| 4,414,127 A * | 11/1983 | Fu | 510/115 |
| 4,655,975 A | 4/1987 | Snoble | |
| 4,826,658 A | 5/1989 | Kay | |
| 4,915,955 A * | 4/1990 | Gomori | 424/616 |
| 5,349,083 A | 9/1994 | Brougham et al. | |
| 5,357,636 A * | 10/1994 | Dresdner et al. | 2/161.7 |
| 5,368,867 A | 11/1994 | Da Silva et al. | |
| 5,419,908 A | 5/1995 | Richter et al. | |
| 5,437,858 A | 8/1995 | Hungerbach et al. | |
| 5,508,046 A | 4/1996 | Cosentino et al. | |
| 5,563,132 A | 10/1996 | Bodaness | |
| 5,709,870 A | 1/1998 | Yoshimura et al. | |
| 5,824,267 A | 10/1998 | Kawasumi et al. | |
| 5,945,032 A * | 8/1999 | Breitenbach et al. | 252/186.29 |
| 5,951,993 A * | 9/1999 | Scholz et al. | 424/405 |
| 5,977,403 A | 11/1999 | Byers | |
| 5,997,585 A | 12/1999 | Scialla et al. | |
| 6,027,469 A | 2/2000 | Johnson | |
| 6,114,298 A | 9/2000 | Petri et al. | |
| 6,197,814 B1 | 3/2001 | Arata | |
| 6,200,946 B1 | 3/2001 | Blum et al. | |
| 6,218,351 B1 | 4/2001 | Busch et al. | |
| 6,231,848 B1 * | 5/2001 | Breitenbach et al. | 424/78.24 |
| 6,242,009 B1 * | 6/2001 | Batarseh et al. | 424/618 |
| 6,257,253 B1 | 7/2001 | Lentsch et al. | |
| 6,277,414 B1 * | 8/2001 | Elhaik et al. | 424/616 |
| 6,302,968 B1 | 10/2001 | Baum et al. | |
| 6,306,812 B1 | 10/2001 | Perkins et al. | |
| 6,368,611 B1 | 4/2002 | Whitbourne et al. | |

(Continued)

FOREIGN PATENT DOCUMENTS

GB 2189394 10/1987

(Continued)

OTHER PUBLICATIONS

Schuster, A. et al., "Persistent silver disinfectant for the environment: Myth and reality," Am. J. Infect. Control, Jun. 2003, pp. 309-311, vol. 32.

(Continued)

*Primary Examiner*—Charles I Boyer
(74) *Attorney, Agent, or Firm*—Thorpe North & Western LLP

(57) ABSTRACT

The present invention is drawn to methods of treating disease or injury. In particular, the invention provides methods for treating viral infections, bacterial infections, fungal infections, and cancerous tissue. The methods include the administration of an aqueous composition that can comprise an aqueous vehicle, including water, from 0.0001 wt % to 10.0 wt % of a peroxygen, and optionally, an alcohol. Additionally, from 0.0001 ppm to 50,000 ppm by weight of a transition metal based on the aqueous vehicle content can also be present. Alternatively or additionally, the transition metal can be in the form of a colloidal transition metal, such as colloidal silver or alloy thereof.

167 Claims, No Drawings

U.S. PATENT DOCUMENTS

| | | | |
|---|---|---|---|
| 6,379,712 B1 | | 4/2002 | Yan et al. |
| 6,436,342 B1 | | 8/2002 | Petri et al. |
| 6,540,791 B1 | * | 4/2003 | Dias .............................. 8/111 |
| 6,569,353 B1 | * | 5/2003 | Giletto et al. .......... 252/186.28 |
| 6,583,176 B2 | | 6/2003 | Arata |
| 6,630,172 B2 | | 10/2003 | Batarseh |
| 6,660,289 B1 | * | 12/2003 | Wilmotte et al. ............ 424/405 |
| 6,743,348 B2 | | 6/2004 | Holladay et al. |
| 6,797,302 B1 | | 9/2004 | Ben Yehuda et al. |
| 6,827,766 B2 | | 12/2004 | Carnes et al. |
| 6,939,564 B2 | | 9/2005 | Ranger et al. |
| 6,939,566 B2 | | 9/2005 | Batarseh et al. |
| 6,962,714 B2 | | 11/2005 | Hei et al. |
| 7,033,511 B2 | * | 4/2006 | Zawada et al. .............. 210/764 |
| 2002/0137648 A1 | | 9/2002 | Sharma et al. |
| 2003/0008797 A1 | | 1/2003 | Hage et al. |
| 2003/0099717 A1 | * | 5/2003 | Cabrera ...................... 424/616 |
| 2003/0235623 A1 | * | 12/2003 | Van Oosterom ............ 424/616 |
| 2004/0067159 A1 | | 4/2004 | Carnes et al. |
| 2004/0170742 A1 | * | 9/2004 | Ben Yehuda et al. ........ 426/615 |
| 2004/0234569 A1 | | 11/2004 | Nakada et al. |
| 2005/0013836 A1 | | 1/2005 | Raad |
| 2005/0194357 A1 | | 9/2005 | Liu et al. |
| 2005/0256017 A1 | | 11/2005 | Dykstra |
| 2005/0256200 A1 | | 11/2005 | Burkhart et al. |
| 2006/0035808 A1 | | 2/2006 | Ahmed et al. |
| 2006/0122082 A1 | | 6/2006 | Paul |
| 2006/0182813 A1 | | 8/2006 | Holladay |
| 2006/0198798 A1 | | 9/2006 | Tichy et al. |
| 2006/0198876 A1 | | 9/2006 | Tichy et al. |
| 2006/0199752 A1 | | 9/2006 | Tichy et al. |
| 2006/0240381 A1 | * | 10/2006 | Rizoiu et al. .................. 433/80 |
| 2006/0263239 A1 | | 11/2006 | Tichy et al. |
| 2007/0048175 A1 | | 3/2007 | Tichy et al. |
| 2007/0053850 A1 | | 3/2007 | Tichy et al. |
| 2007/0059202 A1 | | 3/2007 | Tichy et al. |
| 2007/0254044 A1 | * | 11/2007 | Karandikar et al. ......... 424/618 |
| 2008/0000931 A1 | | 1/2008 | Tichy et al. |

FOREIGN PATENT DOCUMENTS

| | | |
|---|---|---|
| WO | WO 03/080231 | 10/2003 |
| WO | WO 2005/000324 | 1/2005 |
| WO | 2006/079109 | 7/2006 |

OTHER PUBLICATIONS

Brady, Michael J. et al., "Persistent silver disinfectant for the environmental control of pathogenic bacteria," Am. J. Infect. Control, Aug. 2004, pp. 208-214, vol. 31 (4).

Brentano, Loreno et al., "Antibacterial efficacy of a colloidal silver complex," Surg. Forum, 1966, pp. 76-78, vol. 17.

Phillips, Charles R., et al., "Chemical Disinfectant," Annual Review of Microbiology, Oct. 1958, pp. 525-550, vol. 12.

Monarca, S. et al, "Decontamination of dental unit waterlines using disinfectants and filters," Abstract Only, Minerva Stomatol., Oct. 2002, vol. 10.

Yin, Huiyong, "Analysis of Diacyl Peroxides by Ag+ Coordination Ionspray Tandem Mass Spectrometry: Free Radical Pathways of Complex Decomposition," J. Am. Soc. Mass Spectrum, Apr. 2001, pp. 449-455, vol. 12 (4).

http://web.archive.org/web/20060217191603/http://sanosilbiotech.com/start_food.html, Virosil F&B, "Swift Virucidal with Swiss Precision," Feb. 17, 2006, 5 pages.

U.S. Appl. No. 11/891,316, filed Aug. 8, 2007, Tichy et al.

The interaction of silver ions and hydrogen peroxide in the inactivation of E coli: a preliminary evaluation of a new long lasting residual drinking water disinfectant; Water Science and Technology vol. 31 No. 5-6 pp. 123-129 (1995).

Surdeau, N. et al., Sensitivity of bacterial viofilms and planktonic cells to a new antimicrobial agent, Oxsil 320N, Journal of Hospital Infection2006, 62, 487-493, www.elsevierhealth.com/journals/jhin.

* cited by examiner

ND COMPOSITIONS FOR
TREATING VIRAL, FUNGAL, AND
BACTERIAL INFECTIONS

The present application is a continuation-in-part of U.S. patent application Ser. Nos. 11/361,836; 11/361,841; 11/361,837; and 11/361,665 now U.S. Pat. No. 7,351,684, each of which was filed on Feb. 24, 2006, and each of which claims the benefit of U.S. Provisional Patent Application No. 60/656,723, filed on Feb. 25, 2005.

FIELD OF THE INVENTION

The present invention is drawn to therapeutic aqueous compositions which are useful in treating a variety of diseases or injuries including cancer, bacterial disease and infection, viral disease and infection, and fungal and yeast disease and infection.

BACKGROUND OF THE INVENTION

There are a variety of diseases which can debilitate humans and other animals including cancer, bacterial infection, viral infection, and fungal infection. Science and medicine are continually searching for better and more effective methods and compositions for curing or alleviating these diseases and their associated effects. Many times, the diseases can develop in concert with each other, one pathogen attacking one part of the subject while a separate pathogen attacks another. Unfortunately, many treatments are very disease or pathogen dependent and as such not all treatments are effective. As such research continues in an effort to discover new and effective therapeutic compositions and methods which can be used in the treatment of a variety of diseases and disorders.

SUMMARY OF THE INVENTION

In accordance with this, a method of treating a subject for viral infection can comprise administering an aqueous composition to the subject in an amount sufficient to prevent or treat the viral infection. In another embodiment, a method of treating a subject for bacterial infection can comprise administering an aqueous composition to the subject in an amount sufficient to prevent or treat the bacterial infection. In another embodiment, a method of treating a subject for fungal infection can comprise administering an aqueous composition to the subject in an amount sufficient to prevent or treat the fungal infection. For each of these embodiments, whether treatment is as a prophylactic or to ameliorate the disease or injury after infection, the composition can comprise an aqueous vehicle, including water, from 0.0001 wt % to 10.0 wt % of a peroxygen, and optionally, an alcohol. From 0.0001 ppm to 50,000 ppm by weight of a transition metal or alloy thereof based on the aqueous vehicle content can also be present.

In another embodiment, a method for treating cancerous tissue in a subject is also provided. The method includes administering to the subject afflicted with the cancerous tissue a therapeutically effective amount of an aqueous composition. The composition includes an aqueous vehicle with water; from 0.0001 wt % to 10.0 wt % of a peroxygen; and optionally, an alcohol. The composition further includes from 0.0001 ppm to 50,000 ppm by weight of a transition metal or alloy thereof based on the aqueous composition content.

Additional features and advantages of the invention will be apparent from the detailed description that follows, which illustrates, by way of example, features of the invention.

DETAILED DESCRIPTION OF THE PREFERRED EMBODIMENT(S)

Reference will now be made to the exemplary embodiments, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention. It is also to be understood that the terminology used herein is used for the purpose of describing particular embodiments only. The terms are not intended to be limiting unless specified as such.

It must be noted that, as used in this specification and the appended claims, the singular forms "a," "an," and "the" include plural referents unless the content clearly dictates otherwise.

The term "peroxygen" refers to any compound containing a dioxygen (O—O) bond. Dioxygen bonds, particularly bivalent O—O bonds, are readily cleavable, thereby allowing compounds containing them to act as powerful oxidizers. Non-limiting examples of classes of peroxygen compounds include peracids, peracid salts, and peroxides such as hydrogen peroxide.

When referring to the term "alloy," it is understood that individual colloidal or metallic particles can be in the form of composites of multiple metals, or alloys can also include co-dispersions of multiple metals as separate particles.

The term "subject" refers to any animal. In particular, subjects can be mammals, and more particularly humans.

Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a weight ratio range of about 1 wt % to about 20 wt % should be interpreted to include not only the explicitly recited limits of 1 wt % and about 20 wt %, but also to include individual weights such as 2 wt %, 11 wt %, 14 wt %, and sub-ranges such as 10 wt % to 20 wt %, 5 wt % to 15 wt %, etc.

The present invention provides methods for treating and/or preventing certain diseases, or infections related injured tissue. In one embodiment, the invention provides a method for treating subjects afflicted with or at risk of obtaining a viral infection by administering a therapeutic aqueous composition containing a peroxygen, a transition metal, and optionally, an alcohol. In another embodiment, the invention provides a method for treating subjects afflicted with or at risk of obtaining a bacterial infection by administering a therapeutic aqueous composition containing a peroxygen, a transition metal, and optionally, an alcohol. In still another embodiment, the invention provides a method for treating subjects afflicted with or at risk of obtaining a fungal infection by administering a therapeutic aqueous composition containing a peroxygen, a transition metal, and optionally, an alcohol. In another embodiment, the invention provides a method for treating subjects having cancerous tissue by administering a therapeutic aqueous composition containing a peroxygen, a transition metal, and optionally, an alcohol.

The administration of the therapeutic aqueous composition can be done in any acceptable manner known in the medical and pharmaceutical arts. Specific non-limiting examples administration methods which may be used in accordance with embodiments of the present invention include oral administration, injection, topical administration, intravenous administration, etc. Topical administration can be carried out using sprays, mists, lotions, creams, ointments, or gels which are formulated to include the aqueous composition of the present invention. Submersion of the diseased or otherwise infected tissue is also an acceptable means of topical administration. The mode of administration can be dependent on the disease or infection being treated and the formulated potency of the therapeutic aqueous composition. For example, when a bacterial skin infection is treated, it may be desirable to use topical administration of the aqueous composition, whereas, when an internal or subcutaneous tumor is the intended treatment target, injection or oral administration may be a desired mode of administration.

As stated above, the present invention related to methods of treating (including prophylactically treating) viral infections, bacterial infections, or cancerous tissue. Examples of viral infections which may be treated using the methods of the present invention include, without limitation, molluscum contagiosum infection, HTLV infection, HTLV-1 infection, HIV/AIDS infection, human papillomavirus infection, herpesvirus infection, genital herpes infection, viral dysentery, flu, measles, rubella, chickenpox, mumps, polio, rabies, mononucleosis, ebola, respiratory syncytial virus, dengue fever, yellow fever, lassa fever, arena virus, bunyavirus, filovirus, flavivirus, hantavirus, rotavirus, viral meningitis, west Nile fever, arbovirus, parainfluenza, smallpox, epstein-barr virus, dengue hemorrhagic fever, cytomegalovirus, infant cytomegalic virus, progressive multifocal leukoencephalopathy, viral gastroenteritis, a hepatitis, cold sores, ocular herpes, meningitis, encephalitis, shingles, encephalitis, california serogroup viral, St. Louis encephalitis, rift valley fever, hand, foot, & mouth disease, hendra virus, enteroviruses, astrovirus, adenoviruses, Japanese encephalitis, lymphocytic choriomeningitis, roseola infantum, sandfly fever, SARS, warts, cat scratch disease, slap-cheek syndrome, orf, pityriasis rosea, lyssavirus, and the like. Other viruses that can be treated include small pox, H5N1 virus (bird flu), or human papaloma virus.

Examples of bacterial infections which can be treated and prevented using the methods of the present invention include, without limitation, *e. coli* infections (e.g. urinary tract), *Yersinia pestis* (pneumonic plague), *staphyloccal* infection, *streptococcal* infection, *mycobacteria* infection, bacterial pneumonia, snigella dysentery, *serrate* infection, *candida* infection, *cryptococcal* infection, and the like. Other specific examples include methicillin resistant *staphylococcus aureus*, anthrax, or tuberculosis.

Examples of fungal infection which can be treated and prevented using the methods of the present invention include thrush, candidiasis, cryptococcosis, histoplasmosis, blastomycosis, aspergillosis, coccidioidomycosis, paracoccidiomycosis, sporotrichosis, zygomycosis, chromoblastomycosis, lobomycosis, mycetoma, onychomycosis, piedra pityriasis versicolor, tinea barbae, tinea capitis, tinea corporis, tinea cruris, tinea favosa, tinea nigra, tinea pedis, otomycosis, phaeohyphomycosis, or rhinosporidiosis. Yeast infections can also be treated and prevented.

The present invention also provides methods for treating cancerous tissue in a subject. The present invention has been shown to be effective at reducing the size of and even eliminating cancerous tumors. The types of cancers which can be treated using the methods of the present invention include, without limitation, breast cancer, prostate cancer, lung and/or bronchus cancers, colon and rectum cancers, urinary bladder cancer, melanomas of the skin, pancreatic cancer, ovarian cancer, thyroid cancer, stomach cancer, brain cancer, cervical cancer, testicular cancer, lymphomas, cancers of the blood, cancer of the bones and joints, and the like.

The amounts of the therapeutic aqueous compositions which can be administered using the methods of the present invention can vary depending on the type and location of the targeted infection, the mode of administration, and the potency or concentration of the aqueous composition administered. For example, when administered topically using a spray or submersion administration mode for topical local effect, the amount of aqueous composition may not be as important, but rather, the concentration of the aqueous composition and the frequency of administration may be more significant. In one embodiment, the administration can occur one or more times daily for a period of 1 day to 180 days. In another embodiment, the administration can occur one or more times daily for a period of 1 to 7 days. In another embodiment, the administration can occur one or more times for a period of 4 hours to 24 hours.

As mentioned previously, the aqueous composition for use in treating the bacterial and viral infections as well as cancerous tissue can comprise an aqueous vehicle comprising water, from 0.0001 wt % to 10.0 wt % of a peroxygen, and an alcohol. Additionally, from 0.0001 ppm to 50,000 ppm by weight of a transition metal based on the aqueous vehicle content can also be present. It is noted that the lower end of the range of the peroxygen in the administered aqueous composition can be modified to 0.05 wt % or 0.1 wt %, and/or the upper end of the range can be modified to 5 wt %, 3 wt %, or 1.5 wt % in accordance with specific embodiments of the present invention. It is also noted that the alcohol, when present, is given herein without a range limitation, but in one embodiment, can be present at from 0.0001 wt % to 95 wt %. This being stated, the lower end of the range of the alcohol can be modified to 0.05 wt % or 0.1 wt %, and the upper end of the range can be modified to 40 wt %, 30 wt %, 20 wt % or 10 wt % in accordance with specific embodiments of the present invention. Further, the concentration of the metal content, including ionic and/or colloidal content, can also be modified to 10 ppm, 1 ppm, 0.1 ppm, 0.01, or 0.001 by weight at the lower end of the range, and/or to 10,000 ppm, 5,000 ppm, or 1,500 ppm by weight at the upper end of the range. As these ranges are merely exemplary, one skilled in the art could modify these ranges for a particular application, considering such things as the type of alcohol (polyhydric, mixtures, etc.); the type of peroxygen (peroxide, peracid, combination of peroxide/peracid, etc.); the type of metal (ionic, colloidal, alloy, etc.), and particular indication being treated. Further, it is noted that any combination of these upper and lower limits for each of the ingredients are included herein.

The aqueous vehicle can optionally include other ingredients, such as organic co-solvents, so long as the additional ingredients are compatible with the intended method of administration. For example, if the aqueous composition is intended for injection or oral administration it the additional ingredients should be biologically safe or present only in limited biologically safe amounts.

The alcohols in the administered aqueous composition can vary, but in particular, aliphatic alcohols and other carbon-containing alcohols, having from 1 to 24 carbons ($C_1$-$C_{24}$ alcohol) can be included. It is to be noted that "$C_1$-$C_{24}$ alcohol" does not necessarily imply only straight chain saturated aliphatic alcohols, as other carbon-containing alcohols can also be used within this definition, including branched aliphatic alcohols, alicyclic alcohols, aromatic alcohols, unsaturated alcohols, as well as substituted aliphatic, alicyclic, aromatic, and unsaturated alcohols, etc. In one embodiment, the aliphatic alcohols can be $C_1$ to $C_5$ alcohols including methanol, ethanol, propanol and isopropanol, butanols, and pentanols, although as described above, the presence of and the amount of each alcohol will depend on the particular indication being treated and the administration type. Other alcohol types which can also be used include polyhydric alcohols. In some cases polyhydric alcohols can act to enhance the therapeutic power of the aqueous composition. Examples of polyhydric alcohols which can be used in the aqueous composition of the present invention include but are not limited to ethylene glycol (ethane-1,2-diol) glycerin (or glycerol, propane-1,2,3-triol), and propane-1,2-diol. Other non-aliphatic alcohols may also be used including but not limited to phenols and substituted phenols, erucyl alcohol, ricinolyl alcohol, arachidyl alcohol, capryl alcohol, capric alcohol, behenyl alcohol, lauryl alcohol (1-dodecanol), myristyl alcohol (1-tetradecanol), cetyl (or palmityl) alcohol (1-hexadecanol), stearyl alcohol (1-octadecanol), isostearyl alcohol, oleyl alcohol (cis-9-octadecen-1-ol), palmitoleyl alcohol, linoleyl alcohol (9Z,12Z-octadecadien-1-ol), elaidyl alcohol (9E-octadecen-1-ol), elaidolinoleyl alcohol (9E,12E-octadecadien-1-ol), linolenyl alcohol (9Z,12Z,15Z-octadec-atrien-1-ol), elaidolinolenyl alcohol (9E,12E,15E-octadec-atrien-1-ol), combinations thereof, and the like. One skilled in the art would recognize that not all alcohols can be used in all embodiments or in all ranges of amounts due to their toxicity.

In some embodiments, for practical considerations, methanol, ethanol, and denatured alcohols (mixtures of ethanol and smaller amounts of methanol) can often be preferred for use because of their availability and cost. Glycerol is also desirable for use in some embodiments. In one embodiment, ethanol can be preferred. When considering the amount of alcohol to use, one skilled in the art can stay within the above-described ranges, or modify these ranges for a particular application, considering such things as whether alcohol selected for use is polyhydric, whether the alcohol is biologically safe, mixtures of alcohols, etc.

With regard to the transition metal present in the therapeutic aqueous composition of used in the methods of the present invention, the metal can be in ionic form (e.g. disassociate metal salt, metal ions from elemental metal, etc.) and/or in colloidal form. In one specific embodiment, the transition metal can be in a sub-micron form (i.e. dispersion of less than 1 μm metal colloidal particles). However, larger colloidal transition metal particles can also be used in certain applications. Typical transition metals that are desirable for use include Group VI to Group XI transition metals, and more preferably, can include Group X to Group XI transition metals. Alloys including at least one metal from the Group VI to Group XI metals can also be used. It is recognized that any of these metals will typically be oxidized to the corresponding cation in the presence of a peroxygen. However, with colloidal metals, typically, the surface is usually more susceptible to such oxidation. Further, when colloidal metals are dispersed in a colloidal solution, there is often an amount of the metal in ionic or salt form that is also present in the suspension solution. For example, colloidal silver may include a certain percentage of silver salt or ionic silver in solution, e.g., 10% to 90% by weight of metal content can be ionic based on the total metal content. This being stated, certain preferred metals for use in accordance with embodiments of the present invention are ruthenium, rhodium, osmium, iridium, palladium, platinum, copper, gold, silver, manganese, zinc, alloys thereof, and mixtures thereof. Silver is often the most preferred, but metal choice can be dependent to some degree on the application, the levels of kill desired or required, the type of pathogen being targeted, the substrate that is being cleaned, etc.

It is also noted that any of these embodiments can often also benefit from the use of alloys. For Example, certain combinations of metals in an alloy may provide enhanced therapeutic efficacy for particular pathogens or disorders. Preferred examples of transition metal alloys for use in the present invention include but are not limited to copper-silver alloys, silver-manganese alloys, iron-copper alloys, chromium-silver alloys, gold-silver alloys, magnesium-silver alloys, and the like.

Exemplary colloidal silvers that can be used in the therapeutic aqueous composition of the present invention include but are not limited to those sold by Solutions IE, Inc. under the trade names CS Plus and CS Ultra. Other colloidal silver products that can be used as the silver source include ASAP, Sovereign Silver, Silver Max, and the like. In one embodiment, the colloidal particles used in the aqueous composition can have a particle size range of from 0.0001 μm to 1.0 μm. In another embodiment the colloidal transition metal particles can have a size range of from 0.030 μm to 0.5 μm. In still another embodiment the average particle size is 0.35 μm to 0.45 μm. If used in ionic form, preferred silver salts include but are not limited to silver nitrate, silver acetate, silver citrate, silver oxide, and/or silver carbonate.

The peroxygen component of the aqueous composition used in the methods of the present invention can be a single compound or a combination of multiple peroxygen compounds or peroxygen forming compounds. In one embodiment, the peroxygen can be any aliphatic or aromatic peracid. While any functional peroxyacid can be used, peroxyacids containing from 1 to 7 carbons are the most practical for use. These peroxyacids can include, but not be limited to, peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, and/or peroxybenzoic acid. It is noteworthy, that when the peroxygen component of the aqueous composition includes a peracid, the amount of the peracid that may be present cannot reach the upper limits for the peroxygen component. Such amounts of peracid compounds might render the aqueous composition unsafe for biological use. However, one skilled in the art would readily be able to determine biologically safe amounts for any peracid used, and total amounts of peracid compounds used in the aqueous composition.

The peroxyacid included in the aqueous composition used present invention can be prepared using any method known in the art. When the peroxyacid is prepared from an acid and hydrogen peroxide, the resultant mixture contains both the peroxyacid and the corresponding acid that it is prepared from. For example, in embodiments that utilize peroxyacetic acid, the presence of the related acid (acetic acid) provides stability to the mixture, as the reaction is an equilibrium between the acid, hydrogen peroxide, and the peroxyacid and water, as follows:

Peracid salts, such as salts of the above listed peracids, can also be included as the peroxygen component of aqueous compositions used in the present invention. Non-limiting examples of such salts include permanganates, perborates, perchlorates, peracetates, percarbonates, persulphates, and the like. The salts can be used alone or in combination with each other or other peroxygen compounds to form the peroxygen component of the invention.

In another embodiment, the peroxygen component of the invention can be a peroxide compound, or include a peroxide compound. While hydrogen peroxide is considered to be a desirable peroxide for use in accordance with embodiments of the present invention, other peroxides can also be used, such as metal peroxides and peroxyhydrates. The metal peroxides that can be used include, but are not limited to, sodium peroxide, magnesium peroxide, calcium peroxide, barium peroxide, and/or strontium peroxide. As mentioned above, the peroxides can be used alone or in combination with other peroxygen compounds to form the peroxygen component of the present invention. As with the peracids, biologically safe amounts of peroxides could be readily determined by one of ordinary skill in the art.

The aqueous compositions used in the methods of the present invention can be incorporated with other ingredients to form a variety of products for administration including but not limited to ointments, creams, mouth rinses, gels, lozenges or gums for application to the mouth and throat, wipes for skin application, dermal patches, foams, powders and aerosols for topical or inhalation application, bandage dressings, etc. To illustrate one type of application, therapeutic aqueous compositions of the present invention can be formulated into a gel, cream, or ointment for topical application. When formulated as a gel or ointment, the composition can include other excipients and fillers such gelling or thickening agents. Examples of gelling or thickening agents include but are not limited to natural gum such as guar and guar derivatives, a synthetic polymer, a clay, an oil, a wax, aloe vera gel, an acrylate homopolymer, an acrylate copolymer, a carbomer, cellulose, a cellulose derivative, algin, an algin derivative, a water-insoluble $C_8$-$C_{20}$ alcohol, carrageenan, fumed silica, mixtures thereof, and the like. Other excipients common to cream, gel and ointment formulations may also be included. Such excipients and their use are well known to those of ordinary skill in the art. The ointment, gel or cream formulation can be useful in treating both bacterial and viral caused skin infections as well as acting prophylactically to prevent bacterial infection.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

Aqueous Compositions Usable for Treatment or Prevention of Disease or Other Infection An aqueous composition is prepared which includes 0.1 wt % hydrogen peroxide, 4 wt % glycerol, 600 ppm of silver-copper alloy, and the balance water. The aqueous composition is effective in treating/preventing bacterial infections, treating/preventing viral infections, as well as for treating cancerous tissue.

Example 2

Aqueous Compositions Usable for Treatment or Prevention of Disease or Other Infection An aqueous composition is prepare which includes 0.05 wt % peracetic acid, 15 wt % ethanol, 300 ppm of colloidal silver, and the balance water. The aqueous composition is effective in treating/preventing bacterial infections, treating/preventing viral infections, as well as for treating cancerous tissue.

Example 3

Aqueous Compositions Usable for Treatment or Prevention of Disease or Other Infection An aqueous composition is prepared which includes 0.5 wt % peracetic acid, 15 wt % ethanol, 300 ppm of colloidal silver, and the balance water. The aqueous composition is effective in treating/preventing bacterial infections, treating/preventing viral infections, as well as for treating cancerous tissue.

Example 4

Aqueous Compositions Usable for Treatment or Prevention of Disease or Other Infection An aqueous composition is prepared which includes 0.05 wt % hydrogen peroxide acid, 8 wt % ethanol, 150 ppm of colloidal silver, and the balance water. The aqueous composition is effective in treating/preventing bacterial infections, treating/preventing viral infections, as well as for treating cancerous tissue.

Example 5

Aqueous Compositions Usable for Treatment or Prevention of Disease or Other Infection An aqueous composition is prepared which includes 0.05 wt % hydrogen peroxide acid, 150 ppm of colloidal silver, and the balance water. The aqueous composition is effective in treating/preventing bacterial infections, treating/preventing viral infections, as well as for treating cancerous tissue.

Example 6

Aqueous Compositions Usable for Treatment or Prevention of Disease or Other Infection An aqueous composition is prepared with includes 0.05 wt % hydrogen peroxide acid, 0.2 wt % peracetic acid, 400 ppm of colloidal silver, and the balance water. The aqueous composition is effective in treating/preventing bacterial infections, treating/preventing viral infections, as well as for treating cancerous tissue.

Example 7

Treatment of Skin Tumors by Intra-lesional Injection

A rabbit is afflicted with skin tumors. A therapeutic aqueous composition is prepared which has 0.05 wt % hydrogen peroxide, 50 ppm colloidal silver, and the balance water. The rabbit's tumors are injected intra-lesionally with 0.5 ml of the aqueous composition one time. One week after injection with the aqueous composition, the rabbit's tumors are measurably smaller.

Example 8

Treatment of Skin Tumors by Intra-lesional Injection

Same as Example 7, except that the tumor is injected weekly with the aqueous composition until the tumor is no longer detectable.

Example 9

Treatment of Strep Throat Infection

An aqueous composition is prepared which contains 75 ppm colloidal silver, 1 wt % ethanol, 0.4 wt % percitric acid, and the balance water. A subject diagnosed with a strep throat infection gargles and then swallows 1-10 ml of the prepared aqueous composition once every other days for 5 days (3 administrations). Within a day after the 3 administration the strep throat infection is resolved.

Example 10

Treatment of Dog Afflicted with the Parvo Virus

An aqueous composition is prepared which contains 10-100 ppm colloidal silver, 0.05 wt % hydrogen peroxide, and the balance water. A dog afflicted with the Parvo virus receives 8 evenly spaced oral doses of 1-10 ml of the prepared aqueous composition over a 24 hour period. Within 24 hours of the final dose, the dog shows no effects or the infection.

Example 11

Treatment of a Dog with Advanced Skin Infection

An aqueous composition is prepared which contains 10 ppm colloidal silver 0.05 wt % hydrogen peroxide, and the balance water. A dog suffering from an advanced skin infection which has caused rapid necrosis and the onset of kidney failure is treated. Due to the advanced necrosis of the skin, a veterinarian is forced to remove extensive portions of the dogs skin. The afflicted dog receives 1-10 ml/day of the aqueous composition orally, and further, is treated topically 3-4 times a day for 60 days. Within a period of 70 days, the infection is gone and the dog has regrown skin over removed areas without the need of skin grafts.

Example 12

Treatment of Male Infant Afflicted with the Papaloma Virus

A therapeutic aqueous composition is prepared which contains 10 ppm silver, 0.05 wt % hydrogen peroxide, and the balance water. A male infant afflicted with numerous wart patches on both hands who has previously been unsuccessfully treated with other therapeutic remedies receives an injection of the prepared aqueous composition. The infant receives an injection of 0.5 ml of the prepared aqueous composition into one of the wart patches on his hand. Within 10 days, the many of the wart patches on his hands disappear.

Example 13

Treatment of a Burned Tissue Preventing Bacterial Growth

A therapeutic aqueous composition is prepared which contains 100 ppm silver, 0.5 wt % peracetic acid, 6 wt % glycerol, and the balance water. A subject with a third degree burn on the skin is treated with the prepared aqueous composition so as to prevent the onset of bacterial infection at the burned tissue site.

Example 14

Treatment of a Herpes Infection

A therapeutic aqueous composition is prepared which contains 80 ppm a colloidal silver-manganese alloy, 0.1 wt % hydrogen peroxide, 4 wt % ethanol, and the balance water. A subject afflicted with a herpes infection with open sores receives topical treatment using the prepared aqueous composition. The herpes infection is sprayed with the composition daily until the infection is healed.

Example 15

Treatment of a Laceration Preventing Bacterial Growth

A therapeutic aqueous composition is prepared which contains 600 ppm of ionic silver, 0.01 wt % hydrogen peroxide, 40 wt % ethanol, and the balance water. A subject having a sever skin laceration which has become infected receives treatment using the prepared aqueous composition. The composition is topically applied to the laceration once daily for 3 days to reduce or eliminate the bacterial infection.

Example 16

Treatment of a Fungal Infection

A therapeutic aqueous composition is prepared which contains 100 ppm of colloidal silver, 0.1 wt % hydrogen peroxide, 0.4 wt % peracetic acid, 3 wt % isopropyl alcohol, and the balance water. A subject having a fungal infection of the feet is treated by topical application using the prepared aqueous composition. After a daily regimen of treatment for a period of about a week, the no sign of the fungus remains on the skin surface.

While the invention has been described with reference to certain preferred embodiments, those skilled in the art will appreciate that various modifications, changes, omissions, and substitutions can be made without departing from the spirit of the invention. It is therefore intended that the invention be limited only by the scope of the appended claims.

What is claimed is:
1. A method of treating cancerous tissue, comprising:
   administering an aqueous composition to a subject afflicted with cancerous tissue, said aqueous composition comprising:
   a) an aqueous vehicle, including:
      i) water, and
      ii) from 0.0001 wt % to 10.0 wt % of a peroxygen; and
   b) from 0.0001 ppm to 50,000 ppm by weight of a transition metal or alloy thereof based on the aqueous vehicle content.

2. A method as in claim 1, wherein the aqueous composition is administered by injection.

3. A method as in claim 1, wherein the aqueous composition is administered by injection.

4. A method as in claim 1, wherein the aqueous composition is administered topically.

5. A method as in claim 1, wherein the aqueous composition is administered intravenously.

6. A method as in claim 1, wherein the administration is over a period of 1 hour to 7 days.

7. A method as in claim 1, wherein the aqueous composition is formulated for administration in the form of an ointment, cream, mouth rinse, gel, lozenge, gum, wipe, dermal patch, foam, powder, aerosol, or bandage dressings.

8. A method as in claim 1, wherein an alcohol is present in the aqueous composition.

9. A method as in claim 8, wherein the alcohol is present at from 0.001 wt % to 40 wt %.

10. A method as in claim 8, wherein the alcohol is present in the aqueous composition at from 0.1 wt % to 10 wt %.

11. A method as in claim 8, wherein the alcohol is selected from the group consisting of methanol, ethanol, propanols, butanols, pentanols, and mixtures thereof.

12. A method as in claim 8, wherein the alcohol is a polyhydric alcohol.

13. A method as in claim 1, wherein the transition metal or alloy thereof is selected from the group consisting of ruthenium, rhodium, osmium, iridium, palladium, platinum, copper, gold, silver, manganese, zinc, alloys thereof, and mixtures thereof.

14. A method as in claim 1, wherein the transition metal or alloy thereof is a colloidal transition metal or alloy thereof.

15. A method as in claim 14, wherein the colloidal transition metal is colloidal silver.

16. A method as in claim 14, wherein the colloidal transition metal or alloy thereof has an average particle size of from 0.03 µm to 0.5 µm.

17. A method as in claim 1, wherein the transition metal or alloy thereof is an ionic transition metal.

18. A method as in claim 1, wherein the transition metal or alloy thereof is present at from 0.0001 ppm to 1,500 ppm by weight.

19. A method as in claim 1, wherein the peroxygen is a peracid.

20. A method as in claim 19, wherein the peracid is selected from the group consisting of peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, peroxybenzoic acid, and mixtures thereof.

21. A method as in claim 1, wherein the peroxygen is a peroxide.

22. A method as in claim 1, wherein the peroxygen includes a peracid and a peroxide.

23. A method as in claim 1, wherein the peroxygen is present at from 0.05 wt % to 5.0 wt % as part of the aqueous vehicle.

24. A method as in claim 1, wherein the peroxygen is present at from 0.1 wt % to 1.5 wt % as part of the aqueous vehicle.

25. A method as in claim 1, wherein the cancerous tissue is a dermal cancer.

26. A method as in claim 1, wherein the cancerous tissue is prostate cancer.

27. A method as in claim 1, wherein the cancerous tissue is an internal cancer.

28. A method of treating a subject of bacterial, viral, or fungal infection, comprising:
administering an aqueous composition to a subject in an amount sufficient to prevent or treat the viral infection, said aqueous composition comprising:
a) an aqueous vehicle, including:
i) water, and
ii) from 0.0001 wt % to 10.0 wt % of a peroxygen, wherein the peroxygen includes a peracid; and
b) from 0.0001 ppm to 50,000 ppm by weight of a colloidal transition metal or alloy thereof based on the aqueous vehicle content.

29. A method as in claim 28, wherein the aqueous composition is administered orally.

30. A method as in claim 28, wherein the aqueous composition is administered by injection.

31. A method as in claim 28, wherein the aqueous composition is administered topically.

32. A method as in claim 28, wherein the aqueous composition is administered intravenously.

33. A method as in claim 28, wherein the administration is over a period of 1 hour to 7 days.

34. A method as in claim 28, wherein the aqueous composition is formulated for administration in the form of an ointment, cream, mouth rinse, gel, lozenge, gum, wipe, dermal patch, foam, powder, aerosol, or bandage dressings.

35. A method as in claim 28, wherein an alcohol is present in the aqueous composition.

36. A method as in claim 35, wherein the alcohol is present at from 0.001 wt % to 40 wt %.

37. A method as in claim 35, wherein the alcohol is present in the aqueous composition at from 0.1 wt % to 10 wt %.

38. A method as in claim 35, wherein the alcohol is selected from the group consisting of methanol, ethanol, propanols, butanols, pentanols, and mixtures thereof.

39. A method as in claim 35, wherein the alcohol is a polyhydric alcohol.

40. A method as in claim 28, wherein the transition metal or alloy thereof is selected from the group consisting of ruthenium, rhodium, osmium, iridium, palladium, platinum, copper, gold, silver, manganese, zinc, alloys thereof, and mixtures thereof.

41. A method as in claim 28, wherein the colloidal transition metal is colloidal silver.

42. A method as in claim 28, wherein the colloidal transition metal or alloy thereof has an average particle size of from 0.03 µm to 0.5 µm.

43. A method as in claim 28, wherein the transition metal or alloy thereof is present at from 0.0001 ppm to 1,500 ppm by weight.

44. A method as in claim 28, wherein the peracid is selected from the group consisting of peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, peroxybenzoic acid, and mixtures thereof.

45. A method as in claim 28, wherein the peroxygen includes a peroxide.

46. A method as in claim 28, wherein the peroxygen includes a peracid and a peroxide.

47. A method as in claim 28, wherein the peroxygen is present at from 0.05 wt % to 5.0 wt % as part of the aqueous vehicle.

48. A method as in claim 28, wherein the peroxygen is present at from 0.1 wt % to 1.5 wt % as part of the aqueous vehicle.

49. A method as in claim 28, wherein the step of administering is to prevent the viral infection from infecting the subject.

50. A method as in claim 28, wherein the step of administering is to treat the viral infection present in the subject.

51. A method as in claim 28, wherein the viral infection is selected from the group consisting of molluscum contagiosum infection, HTLV infection, HTLV-1 infection, HIV/AIDS infection, human papilloma virus infection, herpes virus infection, genital herpes infection, viral dysentery, flu, measles, rubella, chickenpox, mumps, polio, rabies, mononucleosis, ebola, respiratory syncytial virus, dengue fever, yellow fever, lassa fever, arena virus, bunyavirus, filovirus, flavivirus, hantavirus, rotavirus, viral meningitis, west Nile fever, arbovirus, parainfluenza, smallpox, epstein-barr virus, dengue hemorrhagic fever, cytomegalovirus, infant cytomegalic virus, progressive multifocal leukoencephalopathy, viral gastroenteritis, a hepatitis, cold sores, ocular herpes, meningitis, encephalitis, shingles, encephalitis, california serogroup viral, St. Louis encephalitis, rift valley fever, hand, foot, & mouth disease, hendra virus, enteroviruses, astrovirus, adenoviruses, Japanese encephalitis, lymphocytic choriomeningitis, roseola infantum, sandfly fever, SARS, warts, cat scratch disease, slap-cheek syndrome, orf, pityriasis rosea, or lyssavirus.

52. A method as in claim 28, wherein the virus is small pox.

53. A method as in claim 28, wherein the virus is H5N1 virus.

54. A method as in claim 28, wherein the virus is human papilloma virus.

55. A method as in claim 28, wherein the step of administering is to prevent the bacterial infection from infecting the subject.

56. A method as in claim 28, wherein the subject has a skin injury, and wherein the aqueous composition is applied to the skin injury.

57. A method as in claim 28, wherein the step of administering is to treat the bacterial infection present in the subject.

58. A method as in claim 28, wherein the bacterial infection is selected from the group consisting of *e. coli* infections, *Yersinia pestis, staphylococcal* infection, *streptococcal* infection, *mycobacteria* infection, bacterial pneumonia, *shigella dysentery, serratia* infection, *candida* infection, or *cryptococcal* infection, or tuberculosis.

59. A method as in claim 28, wherein the bacterial infection is methicillin resistant *staphylococcus aureus*.

60. A method as in claim 28, wherein the bacterial infection is anthrax.

61. A method as in claim 28, wherein the step of administering is to prevent the fungal infection from infecting the subject.

62. A method as in claim 28, wherein the step of administering is to treat the fungal infection present in the subject.

63. A method as in claim 28, wherein the fungal infection is selected from the group consisting of thrush, candidiasis, cryptococcosis, histoplasmosis, blastomycosis, aspergillosis, coccidioidomycosis, paracoccidiomycosis, sporotrichosis, zygomycosis, chromoblastomycosis, lobomycosis, mycetoma, onychomycosis, piedra pityriasis versicolor, tinea barbae, tinea capitis, tinea corporis, tinea cruris, tinea favosa, tinea nigra, tinea pedis, otomycosis, phaeohyphomycosis, or rhinosporidiosis.

64. A method as in claim 28, wherein the fungal infection is a yeast infection.

65. A method as in claim 28, wherein the fungal infection is a vaginal infection.

66. A method as in claim 28, wherein the fungal infection is a vaginal infection.

67. A method as in claim 28, wherein the fungal infection is a skin, hair, or nail infection.

68. A method of treating a subject for bacterial, viral, or fungal infection, comprising:
  orally administering an aqueous composition to the subject in an amount sufficient to prevent or treat the viral infection, said aqueous composition comprising:
  a) an aqueous vehicle, including:
    i) water, and
    ii) from 0.0001 wt % to 10.0 wt % of a peroxygen; and
  b) from 0.0001 ppm to 50,000 ppm by weight of a colloidal transition metal or alloy thereof based on the aqueous vehicle content.

69. A method as in claim 68, wherein the administration is over a period of 1 hour to 7 days.

70. A method as in claim 68, wherein the aqueous composition is formulated for oral administration in the form of a gel, lozenge, gum, foam, powder, or aerosol.

71. A method as in claim 68, wherein an alcohol is present in the aqueous composition.

72. A method as in claim 71, wherein the alcohol is present at from 0.001 wt % to 40 wt %.

73. A method as in claim 71, wherein the alcohol is present in the aqueous composition at from 0.1 wt % to 10 wt %.

74. A method as in claim 71, wherein the alcohol is selected from the group consisting of methanol, ethanol, propanols, butanols, pentanols, and mixtures thereof.

75. A method as in claim 71, wherein the alcohol is a polyhydric alcohol.

76. A method as in claim 68, wherein the transition metal or alloy thereof is selected from the group consisting of ruthenium, rhodium, osmium, iridium, palladium, platinum, copper, gold, silver, manganese, zinc, alloys thereof, and mixtures thereof.

77. A method as in claim 68, wherein the colloidal transition metal is colloidal silver.

78. A method as in claim 68, wherein the colloidal transition metal or alloy thereof has an average particle size of from 0.03 μm to 0.5 μm.

79. A method as in claim 68, wherein the transition metal or alloy thereof is present at from 0.0001 ppm to 1,500 ppm by weight.

80. A method as in claim 68, wherein the peracid is selected from the group consisting of peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, peroxybenzoic acid, and mixtures thereof.

81. A method as in claim 68, wherein the peroxygen includes a peroxide.

82. A method as in claim 68, wherein the peroxygen includes a peracid and a peroxide.

83. A method as in claim 68, wherein the peroxygen is present at from 0.05 wt % to 5.0 wt % as part of the aqueous vehicle.

84. A method as in claim 68, wherein the peroxygen is present at from 0.1 wt % to 1.5 wt % as part of the aqueous vehicle.

85. A method as in claim 68, wherein the step of orally administering is to prevent the viral infection from infecting the subject.

86. A method as in claim 68, wherein the viral infection is selected from the group consisting of molluscum contagiosum infection, HTLV infection, HTLV-1 infection, HIV/AIDS infection, human papilloma virus infection, herpes virus infection, genital herpes infection, viral dysentery, flu, measles, rubella, chickenpox, mumps, polio, rabies, mononucleosis, ebola, respiratory syncytial virus, dengue fever, yellow fever, lassa fever, arena virus, bunyavirus, filovirus, flavivirus, hantavirus, rotavirus, viral meningitis, west Nile fever, arbovirus, parainfluenza, smallpox, epstein-barr virus, dengue hemorrhagic fever, cytomegalovirus, infant cytomegalic virus, progressive multifocal leukoencephalopathy, viral gastroenteritis, a hepatitis, cold sores, ocular herpes, meningitis, encephalitis, shingles, encephalitis, california serogroup viral, St. Louis encephalitis, rift valley fever, hand, foot, & mouth disease, hendra virus, enteroviruses, astrovirus, adenoviruses, Japanese encephalitis, lymphocytic choriomeningitis, roseola infantum, sandfly fever, SARS, warts, cat scratch disease, slap-cheek syndrome, orf, pityriasis rosea, or lyssavirus.

87. A method as in claim 68, wherein the virus is small pox.

88. A method as in claim 68, wherein the virus is H5N1 virus.

89. A method as in claim 68, wherein the virus is human papilloma virus.

90. A method as in claim 68, wherein the step of orally administering is to prevent the bacterial infection from infecting the subject.

91. A method as in claim 68, wherein the step of orally administering is to treat the bacterial infection present in the subject.

92. A method as in claim 68, wherein the bacterial infection is selected from the group consisting of *e. coli* infections, *Yersinia pestis, staphylococcal* infection, *streptococcal* infection, *mycobacteria* infection, bacterial pneumonia, *shigella dysentery, serratia* infection, *candida* infection, or *cryptococcal* infection, or tuberculosis.

93. A method as in claim 68, wherein the bacterial infection is methicillin resistant *staphylococcus aureus.*

94. A method as in claim 68, wherein the bacterial infection is anthrax.

95. A method as in claim 68, wherein the step of orally administering is to prevent the fungal infection from infecting the subject.

96. A method as in claim 68, wherein the step of orally administering is to treat the fungal infection present in the subject.

97. A method as in claim 68, wherein the fungal infection is selected from the group consisting of thrush, candidiasis, cryptococcosis, histoplasmosis, blastomycosis, aspergillosis, coccidioidomycosis, paracoccidiomycosis, sporotrichosis, zygomycosis, chromoblastomycosis, lobomycosis, mycetoma, onychomycosis, piedra pityriasis versicolor, tinea barbae, tinea capitis, tinea corporis, tinea cruris, tinea favosa, tinea nigra, tinea pedis, otomycosis, phaeohyphomycosis, or rhinosporidiosis.

98. A method as in claim 68, wherein the fungal infection is a yeast infection.

99. A method as in claim 68, wherein the fungal infection is a vaginal infection.

100. A method as in claim 68, wherein the fungal infection is a skin, hair, or nail infection.

101. A method of treating a subject for bacterial, viral, or fungal infection, comprising:
  intravenously administering an aqueous composition to the subject in an amount sufficient to prevent or treat the viral infection, said aqueous composition comprising:
  a) an aqueous vehicle, including:
    i) water, and
    ii) from 0.0001 wt % to 10.0 wt % of a peroxygen; and
  b) from 0.0001 ppm to 50,000 ppm by weight of a colloidal transition metal or alloy thereof based on the aqueous vehicle content.

102. A method as in claim 101, wherein the intravenous administration is over a period of 1 hour to 7 days.

103. A method as in claim 101, wherein an alcohol is present in the aqueous composition.

104. A method as in claim 103, wherein the alcohol is present at from 0.001 wt % to 40 wt %.

105. A method as in claim 103, wherein the alcohol is present in the aqueous composition at from 0.1 wt % to 10 wt %.

106. A method as in claim 103, wherein the alcohol is selected from the group consisting of methanol, ethanol, propanols, butanols, pentanols, and mixtures thereof.

107. A method as in claim 103, wherein the alcohol is a polyhydric alcohol.

108. A method as in claim 101, wherein the transition metal or alloy thereof is selected from the group consisting of ruthenium, rhodium, osmium, iridium, palladium, platinum, copper, gold, silver, manganese, zinc, alloys thereof, and mixtures thereof.

109. A method as in claim 101, wherein the colloidal transition metal is colloidal silver.

110. A method as in claim 101, wherein the colloidal transition metal or alloy thereof has an average particle size of from 0.03 µm to 0.5 µm.

111. A method as in claim 101, wherein the transition metal or alloy thereof is present at from 0.0001 ppm to 1,500 ppm by weight.

112. A method as in claim 101, wherein the peracid is selected from the group consisting of peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, peroxybenzoic acid, and mixtures thereof.

113. A method as in claim 101, wherein the peroxygen includes a peroxide.

114. A method as in claim 101, wherein the peroxygen includes a peracid and a peroxide.

115. A method as in claim 101, wherein the peroxygen is present at from 0.05 wt % to 5.0 wt % as part of the aqueous vehicle.

116. A method as in claim 101, wherein the peroxygen is present at from 0.1 wt % to 1.5 wt % as part of the aqueous vehicle.

117. A method as in claim 101, wherein the step of intravenously administering is to prevent the viral infection from infecting the subject.

118. A method as in claim 101, wherein the step of intravenously administering is to treat the viral infection present in the subject.

119. A method as in claim 101, wherein the viral infection is selected from the group consisting of molluscum contagiosum infection, HTLV infection, HTLV-1 infection, HIV/AIDS infection, human papilloma virus infection, herpes virus infection, genital herpes infection, viral dysentery, flu, measles, rubella, chickenpox, mumps, polio, rabies, mononucleosis, ebola, respiratory syncytial virus, dengue fever, yellow fever, lassa fever, arena virus, bunyavirus, filovirus, flavivirus, hantavirus, rotavirus, viral meningitis, west Nile fever, arbovirus, parainfluenza, smallpox, epstein-barr virus, dengue hemorrhagic fever, cytomegalovirus, infant cytomegalic virus, progressive multifocal leukoencephalopathy, viral gastroenteritis, a hepatitis, cold sores, ocular herpes, meningitis, encephalitis, shingles, encephalitis, california serogroup viral, St. Louis encephalitis, rift valley fever, hand, foot, & mouth disease, hendra virus, enteroviruses, astrovirus, adenoviruses, Japanese encephalitis, lymphocytic choriomeningitis, roseola infantum, sandfly fever, SARS, warts, cat scratch disease, slap-cheek syndrome, orf, pityriasis rosea, or lyssavirus.

120. A method as in claim 101, wherein the virus is small pox.

121. A method as in claim 101, wherein the virus is H5N1 virus.

122. A method as in claim 101, wherein the virus is human papilloma virus.

123. A method as in claim 101, wherein the step of intravenously administering is to prevent the bacterial infection from infecting the subject.

124. A method as in claim 101, wherein the step of intravenously administering is to treat the bacterial infection present in the subject.

125. A method as in claim 101, wherein the bacterial infection is selected from the group consisting of *e. coli* infections, *Yersinia pestis, staphylococcal* infection, *streptococcal* infection, *mycobacteria* infection, bacterial pneumonia, *shigella dysentery, serratia* infection, *candida* infection, or *cryptococcal* infection, or tuberculosis.

126. A method as in claim 101, wherein the bacterial infection is methicillin resistant *staphylococcus aureus*.

127. A method as in claim 101, wherein the bacterial infection is anthrax.

128. A method as in claim 101, wherein the step of intravenously administering is to prevent the fungal infection from infecting the subject.

129. A method as in claim 101, wherein the step of intravenously administering is to treat the fungal infection present in the subject.

130. A method as in claim 101, wherein the fungal infection is selected from the group consisting of thrush, candidiasis, cryptococcosis, histoplasmosis, blastomycosis, aspergillosis, coccidioidomycosis, paracoccidiomycosis, sporotrichosis, zygomycosis, chromoblastomycosis, lobomycosis, mycetoma, onychomycosis, piedra pityriasis versicolor, tinea barbae, tinea capitis, tinea corporis, tinea cruris, tinea favosa, tinea nigra, tinea pedis, otomycosis, phaeohyphomycosis, or rhinosporidiosis.

131. A method as in claim 101, wherein the fungal infection is a yeast infection.

132. A method as in claim 101, wherein the fungal infection is a vaginal infection.

133. A method as in claim 101, wherein the fungal infection is a skin, hair, or nail infection.

134. A method of treating a subject for bacterial, viral, or fungal infection, comprising:
  administering by injection an aqueous composition to the subject in an amount sufficient to prevent or treat the viral infection, said aqueous composition comprising:
    a) an aqueous vehicle, including:
      i) water, and
      ii) from 0.0001 wt % to 10.0 wt % of a peroxygen; and
    b) from 0.0001 ppm to 50,000 ppm by weight of a colloidal transition metal or alloy thereof based on the aqueous vehicle content.

135. A method as in claim 134, wherein the administration by injection is over a period of 1 hour to 7 days.

136. A method as in claim 134, wherein an alcohol is present in the aqueous composition.

137. A method as in claim 136, wherein the alcohol is present at from 0.001 wt % to 40 wt %.

138. A method as in claim 136, wherein the alcohol is present in the aqueous composition at from 0.1 wt % to 10 wt %.

139. A method as in claim 136, wherein the alcohol is selected from the group consisting of methanol, ethanol, propanols, butanols, pentanols, and mixtures thereof.

140. A method as in claim 136, wherein the alcohol is a polyhydric alcohol.

141. A method as in claim 134, wherein the transition metal or alloy thereof is selected from the group consisting of ruthenium, rhodium, osmium, iridium, palladium, platinum, copper, gold, silver, manganese, zinc, alloys thereof, and mixtures thereof.

142. A method as in claim 134, wherein the colloidal transition metal is colloidal silver.

143. A method as in claim 134, wherein the colloidal transition metal or alloy thereof has an average particle size of from 0.03 µm to 0.5 µm.

144. A method as in claim 134, wherein the transition metal or alloy thereof is present at from 0.0001 ppm to 1,500 ppm by weight.

145. A method as in claim 134, wherein the peracid is selected from the group consisting of peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, peroxybenzoic acid, and mixtures thereof.

146. A method as in claim 134, wherein the peroxygen includes a peroxide.

147. A method as in claim 134, wherein the peroxygen includes a peracid and a peroxide.

148. A method as in claim 134, wherein the peroxygen is present at from 0.05 wt % to 5.0 wt % as part of the aqueous vehicle.

149. A method as in claim 134, wherein the peroxygen is present at from 0.1 wt % to 1.5 wt % as part of the aqueous vehicle.

150. A method as in claim 134, wherein the step of administering by injection is to prevent the viral infection from infecting the subject.

151. A method as in claim 134, wherein the step of administering by injection is to treat the viral infection present in the subject.

152. A method as in claim 134, wherein the viral infection is selected from the group consisting of molluscum contagiosum infection, HTLV infection, HTLV-1 infection, HIV/AIDS infection, human papilloma virus infection, herpes virus infection, genital herpes infection, viral dysentery, flu, measles, rubella, chickenpox, mumps, polio, rabies, mononucleosis, ebola, respiratory syncytial virus, dengue fever, yellow fever, lassa fever, arena virus, bunyavirus, filovirus, flavivirus, hantavirus, rotavirus, viral meningitis, west Nile fever, arbovirus, parainfluenza, smallpox, epstein-barr virus, dengue hemorrhagic fever, cytomegalovirus, infant cytomegalic virus, progressive multifocal leukoencephalopathy, viral gastroenteritis, a hepatitis, cold sores, ocular herpes, meningitis, encephalitis, shingles, encephalitis, california serogroup viral, St. Louis encephalitis, rift valley fever, hand, foot, & mouth disease, hendra virus, enteroviruses, astrovirus, adenoviruses, Japanese encephalitis, lymphocytic choriomeningitis, roseola infantum, sandfly fever, SARS, warts, cat scratch disease, slap-cheek syndrome, orf, pityriasis rosea, or lyssavirus.

153. A method as in claim 134, wherein the virus is small pox.

154. A method as in claim 134, wherein the virus is H5N1 virus.

155. A method as in claim 134, wherein the virus is human papilloma virus.

156. A method as in claim 134, wherein the step of administering by injection is to prevent the bacterial infection from infecting the subject.

157. A method as in claim 134, wherein the step of administering by injection is to treat the bacterial infection present in the subject.

158. A method as in claim 134, wherein the bacterial infection is selected from the group consisting of *e. coli* infections, *Yersinia pestis, staphylococcal* infection, *streptococcal* infection, *mycobacteria* infection, bacterial pneumonia, *shigella dysentery, serrate* infection, *candida* infection, or *cryptococcal* infection, or tuberculosis.

159. A method as in claim 134, wherein the bacterial infection is methicillin resistant *staphylococcus aureus*.

160. A method as in claim 134, wherein the bacterial infection is anthrax.

161. A method as in claim 134, wherein the step of administering by injection is to prevent the fungal infection from infecting the subject.

162. A method as in claim 134, wherein the step of administering by injection is to treat the fungal infection present in the subject.

163. A method as in claim 134, wherein the fungal infection is selected from the group consisting of thrush, candidiasis, cryptococcosis, histoplasmosis, blastomycosis, aspergillosis, coccidioidomycosis, paracoccidiomycosis, sporotrichosis, zygomycosis, chromoblastomycosis, lobomycosis, mycetoma, onychomycosis, piedra pityriasis versicolor, tinea barbae, tinea capitis, tinea corporis, tinea cruris, tinea favosa, tinea nigra, tinea pedis, otomycosis, phaeohyphomycosis, or rhinosporidiosis.

164. A method as in claim 134, wherein the fungal infection is a yeast infection.

165. A method as in claim 134, wherein the fungal infection is a vaginal infection.

166. A method as in claim 134, wherein the fungal infection is a skin, hair, or nail infection.

167. A method as in claim 68, wherein the step of orally administering is to treat the viral infection present in the subject.

* * * * *